US008129523B2

(12) United States Patent
Wilk et al.

(10) Patent No.: US 8,129,523 B2
(45) Date of Patent: Mar. 6, 2012

(54) COUPLING PROCESS FOR GENERATING REACTIVE BORON-CONTAINING DERIVATIVES OF N-SUBSTITUTED PYRROLE-2-CARBONITRILES TO PRODUCE BIARYLS

(75) Inventors: Bogdan Kazimierz Wilk, New City, NY (US); Arkadiy Zinoviy Rubezhov, West Nyack, NY (US); Jean Louise Helom, Hillsdale, NJ (US)

(73) Assignee: Wyeth LLC, Madison, NJ (US)

( * ) Notice: Subject to any disclaimer, the term of this patent is extended or adjusted under 35 U.S.C. 154(b) by 644 days.

(21) Appl. No.: 12/238,530

(22) Filed: Sep. 26, 2008

(65) Prior Publication Data

US 2009/0054663 A1 Feb. 26, 2009

Related U.S. Application Data

(62) Division of application No. 11/113,794, filed on Apr. 25, 2005, now Pat. No. 7,446,211.

(60) Provisional application No. 60/647,656, filed on Jan. 27, 2005, provisional application No. 60/565,636, filed on Apr. 27, 2004.

(51) Int. Cl.
C07D 265/12 (2006.01)

(52) U.S. Cl. .......................................... 544/92

(58) Field of Classification Search ..................... 544/92
See application file for complete search history.

(56) References Cited

U.S. PATENT DOCUMENTS

| | | | |
|---|---|---|---|
| 5,194,628 | A | 3/1993 | Ackermann et al. |
| 6,387,992 | B1 | 5/2002 | Pastor et al. |
| 6,391,907 | B1 | 5/2002 | Fensome et al. |
| 6,407,101 | B1 | 6/2002 | Collins et al. |
| 6,436,929 | B1 | 8/2002 | Zhang et al. |
| 6,444,668 | B1 | 9/2002 | Grubb et al. |
| 6,509,334 | B1 | 1/2003 | Zhang et al. |
| 6,562,857 | B2 | 5/2003 | Collins et al. |
| 6,566,358 | B2 | 5/2003 | Zhang et al. |
| 2002/0065192 | A1 | 5/2002 | MacKenzie et al. |
| 2003/0149273 | A1 | 8/2003 | Militzer et al. |
| 2005/0272702 | A1 | 12/2005 | Wilk et al. |

FOREIGN PATENT DOCUMENTS

| | | |
|---|---|---|
| DE | 10111262 | 9/2002 |
| EP | 1308157 | 5/2003 |
| WO | WO-93/10127 A | 5/1993 |
| WO | WO-95/07275 | 3/1995 |
| WO | WO-00/50470 | 8/2000 |
| WO | WO-00/66571 A | 11/2000 |
| WO | WO-00/66581 A | 11/2000 |
| WO | WO-01/83571 | 11/2001 |
| WO | WO-01/96406 | 12/2001 |
| WO | WO-02/36641 | 5/2002 |
| WO | WO-02/36642 | 5/2002 |
| WO | WO-02/42281 | 5/2002 |
| WO | WO-03/031401 | 4/2003 |
| WO | WO-03/105860 | 12/2003 |

OTHER PUBLICATIONS

International search report for application PCT/US2005/013992, Oct. 24, 2005.*
Fensome, "Design, synthesis, and SAR of new pyrrole-oxindole progesterone receptor modulators leading to 5-(7-fluoro-3,3-dimethyl-2-oxo-2,3-dihydro-1H-indol-5-yl)-1-methyl-1H-pyrrole-2-carbonitrile (WAY-255348)", Journal of Medicinal Chemistry, vol. 51, No. 6, (Mar. 27, 2008; Epub Mar. 5, 2008), pp. 1861-1873.
Bayly, "Structure-based design of COX-2 selectivity into flurbiprofen", BioOrg Med Chem Lett, 9(3):307-312 (Feb. 8, 1999).
Caron, "Directed Ortho Metalation of Neopentyl Benzoates with LDA: Preparation of Arylboronic Acids", J Org Chem, 63(7):2054-2055 (Apr. 3, 1998).
Murase, "A synthesis of arcyriacyanin A, an unsymmetrically substituted indole pigment of the slime mould by palladium catalyzed cross-coupling reaction", Chem Pharm Bull, 46(6):889-892 (Jun. 1998).
Kristensen, "Synthesis of ortho substituted arylboronic esters by in situ trapping of unstable lithio intermediates", Org Lett, 10:1435-1437 (May 17, 2001).
Molander, "Efficient Ligandless Palladium-Catalyzed Suzuki Reactions of Potassium Aryltrifluoroborates", Org Lett, 4:1867-1870 (May 30, 2002).
Vazquez, "A non-cryogenic method for the preparation of 2-(indolyl) borates, silanes, and silanols", J Org Chem, 67(21):7551-7552 (Oct. 18, 2002).
Winkle, "Suzuki Reaction of a Diarylborinic Acid: One-Pot Preparation and Cross-Coupling of Bis(3,5-dimethylphenyl)borinic Acid", Org Proc Res Dev, 5(4):450-451 (Jul. 2001).
Goosen, English Abstract of German Patent No. DE-10111262, Issued: Sep. 12, 2002.
"Products for Suzuki Coupling", ChemFiles, Sigma-Aldrich Co., vol. 1, No. 1, 2001.
"Products for Suzuki Coupling", ChemFiles, Sigma-Aldrich Co., vol. 2, No. 1, 2002.
"Reagents for Suzuki Coupling", ChemFiles, Sigma-Aldrich Co., vol. 3, No. 1, 2002.
"Reagents for C-C Bond Formation", ChemFiles, Sigma-Aldrich Co., vol. 4, No. 2, 2004.

* cited by examiner

*Primary Examiner* — Laura L. Stockton
(74) *Attorney, Agent, or Firm* — Howson & Howson LLP

(57) ABSTRACT

A convenient preparation of boron-containing compounds, borate salts, pyrrolecarbonitrile boron-containing compounds, N-substituted-pyrrole-2-carbonitrile boron-containing compounds, and derivatives thereof is provided. The present invention also provides for the use of these boron-containing compounds and derivatives thereof in coupling reactions to provide bi-aryl compounds.

3 Claims, No Drawings

COUPLING PROCESS FOR GENERATING REACTIVE BORON-CONTAINING DERIVATIVES OF N-SUBSTITUTED PYRROLE-2-CARBONITRILES TO PRODUCE BIARYLS

CROSS REFERENCE TO RELATED APPLICATIONS

This application is a divisional of U.S. patent application Ser. No. 11/113,794, filed Apr. 25, 2005, now U.S. Pat. No. 7,446,211, issued Nov. 4, 2008, which claims the benefit of the priorities of U.S. Provisional Patent Application No. 60/647,656, filed Jan. 27, 2005, now abandoned, and U.S. Provisional Patent Application No. 60/565,636, filed Apr. 27, 2004, now abandoned.

BACKGROUND OF THE INVENTION

The present invention relates to processes for generating boron-containing compounds and bi-aryls.

The Suzuki-type coupling to form bi-aryl compounds is usually accomplished by reacting boronic acids with aryl moieties having leaving groups such as halogen, triflates, and diazonium salts, among others.

In a typical Suzuki coupling, a N-t-butoxycarbonyl-substituted pyrrole (N-Boc-pyrrole) is first deprotonated using butyllithium compounds. The lithiated N-Boc-pyrrole is then quenched with a trialkylborate, typically triisopropyl borate, and the intermediate reacted with a bromoaryl compound in the presence of a palladium catalyst to couple the aryl and pyrrole moieties. Subsequent cyanation of the pyrrole moiety followed by Boc deprotection and N-methylation gives the coupled product.

This lengthy coupling is plagued by non-selective methylation of the cyano substituent. Further, the intermediates generated during the coupling have been reported to be thermally unstable.

What is needed in the art are alternative methods for coupling aryl compounds.

SUMMARY OF THE INVENTION

In one aspect, methods for preparing 2-cyanopyrrole boron-containing compounds are provided.

In a further aspect, methods for preparing 2-cyanopyrrole boronate and borinate salts, boronic and borinic esters and salts thereof, and boronic and borinic acids and salts thereof, are provided.

In another aspect, methods for preparing 2-cyanopyrrole trifluoroborate salts are provided.

In a further aspect, methods for coupling 2-cyanopyrroles and aryl compounds are provided.

In yet another aspect, the following compounds are provided:

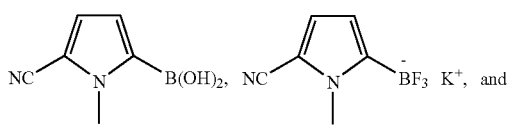

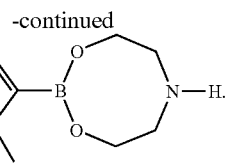

In a further aspect, methods for preparing and purifying 5-(4,4-dimethyl-2-oxo-1,4-dihydro-2H-3,1-benzoxazin-6-yl)-1H-pyrrole-2-carbonitrile are provided.

In still another aspect, methods for preparing and purifying 5-(4,4-dimethyl-2-thioxo-1,4-dihydro-2H-3,1-benzoxazin-6-yl)-1H-pyrrole-2-carbonitrile are provided.

Other aspects and advantages of the present invention are described further in the following detailed description of the preferred embodiments thereof.

DETAILED DESCRIPTION OF THE INVENTION

The present invention provides methods for preparing boron-containing compounds. In one embodiment, the present invention provides methods for preparing N-substituted pyrrole carbonitrile boron-containing compounds. Such compounds include, without limitation, N-substituted pyrrole-2-carbonitrile boron-containing compounds, N-alkyl-pyrrole-2-carbonitrile boron-containing compounds, and N-methyl-pyrrole-2-carbonitrile boron-containing compounds.

Such compounds can be isolated or used in situ in further reactions, such as Suzuki-type coupling, to give pyrrole-containing biaryls.

I. DEFINITIONS

The term "alkyl" is used herein as a group or part of a group refers to both straight- and branched-chain saturated aliphatic hydrocarbon groups having 1 to about 10 carbon atoms, and desirably 1 to about 8, e.g., 6, carbon atoms. The term "alkenyl" is used herein to refer to both straight- and branched-chain alkyl groups having one or more carbon-carbon double bonds and containing 2 to about 10 carbon atoms. Desirably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. Desirably, the term alkynyl refers to an alkyl group having 1 or 2 carbon-carbon triple bonds and having 2 to about 6 carbon atoms.

The term "cycloalkyl" is used herein to refer to an alkyl group as previously described that is cyclic in structure and has about 3 to about 10 carbon atoms, e.g., 3-8 carbon atoms, desirably about 5 to about 3 carbon atoms. The terms "substituted alkyl", "substituted alkenyl", "substituted alkynyl", and "substituted cycloalkyl" refer to alkyl, alkenyl, and alkynyl groups, respectively, having one or more (e.g., 2 or 3) substituents including, without limitation, halogen, CN, OH, NO₂, amino, aryl, heteroaryl, alkoxy, aryloxy, alkylcarbonyl, alkylcarboxy, and arylthio which groups can be optionally substituted. These substituents can be attached to any carbon of an alkyl, alkenyl, alkynyl, or cycloalkyl group provided that the attachment constitutes a stable chemical moiety.

The term "heteroalkyl" is used herein to refer to an alkyl or substituted alkyl group as previously described that contains heteroatoms in the backbone of the alkyl moiety. The heteroalkyl has carbon atoms and one or more heteroatoms including nitrogen, oxygen, and sulfur atoms. Desirably, the heteroalkyl has 1 to about 4 heteroatoms in the backbone of the ring. The heteroalkyl group typically has 1 to about 10 carbon atoms, and desirably 1 to about 8, e.g., 6, carbon atoms.

The term "aryl" as used herein refers to an aromatic system, e.g., of about 6-20 carbon atoms, more particularly 6-14 carbons, which can include a single ring or multiple (e.g., two or three) aromatic rings fused or linked together where at least one part of the fused or linked rings forms the conjugated aromatic system. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. Desirably, a substituted aryl group is substituted with 1 to about 4 substituents.

The term "heteroaryl" and "heterocyclic" can be used interchangeably and are used herein to refer to a stable 4- to 20-membered monocyclic or multicyclic heterocyclic ring which is saturated, partially unsaturated, or wholly unsaturated. Desirably, the monocyclic heterocyclic ring is a stable 4- to 7-membered ring. The heteroaryl or heterocyclic ring has carbon atoms and one or more heteroatoms including nitrogen, oxygen, and sulfur atoms. Desirably, the heteroaryl or heterocyclic ring has 1 to about 4 heteroatoms in the backbone of the ring. When the heteroaryl or heterocyclic ring contains nitrogen or sulfur atoms in the backbone of the ring, the nitrogen or sulfur atoms can be oxidized. The term "heteroaryl" or "heterocyclic" also refers to multicyclic rings in which a heteroaryl or heterocyclic ring is fused to an aryl ring. The heteroaryl or heterocyclic ring can be attached to the is aryl ring through a heteroatom or carbon atom provided the resultant heterocyclic ring structure is chemically stable.

A variety of heteroaryl or heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heteroaryl" or "substituted heterocyclic" as used herein refers to a heteroaryl or heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. Desirably, a substituted heteroaryl or heterocyclic group is substituted with 1 to about 4 substituents.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" as used herein refers to the alkyl OH group, where the point of attachment is through the alkyl group and the alkyl group is optionally substituted.

The term "arylthio" as used herein refers to the S(aryl) group, where the point of attachment is through the sulfur-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The term "acyl" as used herein refers to an alkyl or substituted alkyl group as just described having a carbonyl group, i.e., C(=O) group, in the backbone of alkyl moiety.

The term "sulfonyl" as used herein refers to an alkyl or substituted alkyl group as just described having a sulfonyl group, i.e., $SO_2$ group in the backbone of the alkyl moiety.

The term "leaving group" as used herein refers to a substituent that is present on a chemical compound and can be displaced (the term L as used herein refers to a leaving group). The particular leaving group utilized in the present invention is dependent upon the specific reaction being performed and can readily be determined by one of skill in the art. Common leaving groups include, without limitation, halides and sulfonates ($OSO_2R'$), whereby R' is an alkyl. Desirably, the leaving group is a halide such as bromine, chlorine, or iodine, and more desirably is bromine.

The term "organometallic coupling agent" as used herein refers to compound that contains a transition metal and one or more ligands attached thereto. A variety of transition metals can be used in the present invention and include Pd and Ni metals, among others. Several ligands can be bound to the transition metal and include, without limitation, acetate, hydroxyl, nitrile, halide, and phosphine substituents. Many transition metal complexes containing such ligands are commercially available and include those recited on the Strem Chemical, Inc. website. Desirably, the organometallic coupling agent is selected from among tetrakis(triphenylphosphine)palladium, Bis(tri-tert-butylphosphine)palladium(0), Tris(dibenzylideneacetone)dipalladium(0), Dichloro[1,1'-bis(diphenylphosphino)ferrocene]palladium(II), trans-Dichlorobis(triphenylphosphine)palladium(II), Palladium (II)acetate, Palladium(II) chloride, Palladium on carbon, Dichloro[1,1'-bis(diphenylphosphino)ferrocene]nickel(II), and Bis(triphenylphosphine)nickel(II) chloride.

As used herein, the term "strong non-nucleophilic base" refers to a compound that is capable of removing a H-atom attached to a carbon-atom (designated $CC^+base^-$ in the description and schemes). Desirably, the strong non-nucleophilic base can remove a H-atom from a pyrrole ring, but not react with the other substituents on the ring, if so present. Desirably, the strong non-nucleophilic base can remove a H-atom from the 5-position of a pyrrole ring. A variety of strong non-nucleophilic bases is known to those of skill in the art and include diisopropyl amine salts. See, the strong non-nucleophilic bases on the FMC Lithium website. In one embodiment, the strong nucleophilic base is lithium diisopropyl amide (LDA).

The term "boron agent" as used herein refers to a neutral compound that contains a boron atom (designated $BR_3$ or $B(O\text{-subst})_3$ in the schemes). Typically, the boron agent has 1, 2, or 3 substituents. Desirably, the substituents (abbreviated "subst" herein and in the schemes) are bound directly to the boron atom or through an O-atom.

The term "borate salt" as used herein refers to a compound containing a boron atom and is present as a salt including boronate and borinate salts. Derivatives of borate salts include, without limitation, both neutral and charged compounds including boronic esters, borinic esters, boronic acids, or borinic acids.

The term "boronate ester salt" as used herein refers to a compound having a —B(O-substituent)$_3$ or —B(substituent)$_3$ group attached thereto, wherein the substituent forms a stable bond. The term "boronate ester" also refers to a compound having the a —B[—O—$R^{19}$—O—] group attached thereto, wherein the boron atom is bound to the compound and to the two O-atoms, where $R^{19}$ is defined below.

The term "borinate ester salt" as used herein refers to a compound having a —B(O-substituent)$_2$- or —B(substituent)$_2$-group attached thereto, wherein the substituent forms a stable bond to an O-atom attached to the boron atom and the boron atom is attached to the compound through 2 bonds.

The term "boronic ester" as used herein refers to a compound having a —B(O-substituent)$_2$ group attached thereto, wherein the substituent forms a stable bond to an O-atom attached to the boron atom. The term "boronic ester" also refers to a compound having a —B[—O—$R^{19}$—O—] group attached thereto, wherein the boron atom is bound to the compound and to the two O-atoms, where $R^{19}$ is defined below.

The term "borinic ester" as used herein refers to a compound having a —B(O-substituent)-group attached thereto, wherein the substituent forms a stable bond to an O-atom attached to the boron atom and the boron atom is attached to the compound through 2 bonds.

The term "boron compound" as used herein refers to a neutral compound prepared according to the present invention having a —B(substituent)$_2$ or —B(substituent)-group attached thereto, wherein the substituent forms a stable bond to the boron-atom.

The term "boronic acid" as used herein refers to a compound having a —B(OH)$_2$ group attached thereto.

The term "borinic acid" as used herein refers to a compound having a —B(OH)— group attached thereto and the boron atom is attached to the compound through 2 bonds.

The term "catalyst scavenger" as used herein refers to a compound or complex that removes a catalyst from a solution containing the catalyst.

II. METHODS OF PREPARING BORON-CONTAINING COMPOUNDS AND DERIVATIVES THEREOF

The present invention provides methods for preparing boron-containing compounds which can be isolated or used in situ in further reactions. These boron-containing compounds, and derivatives thereof, are defined in detail above and include boronate salts, borinate salts, boronic esters and salts thereof, borinic esters and salts thereof, boronic acids, and borinic acids.

In one embodiment, boronic and borinic esters of formulas (A) and (B) can be prepared according to the invention.

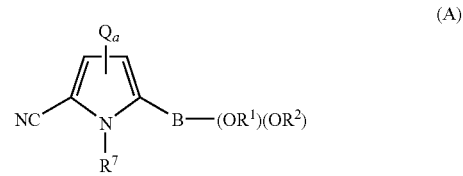

(A)

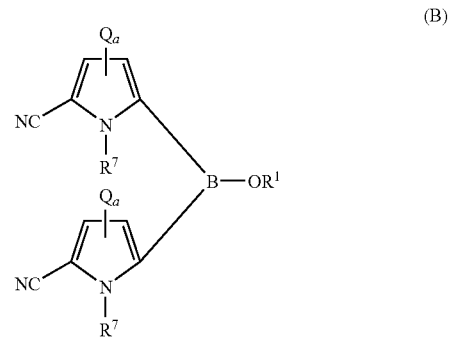

(B)

Certain boron compounds can be prepared according to the present invention and include compounds of formulas (C) and (D).

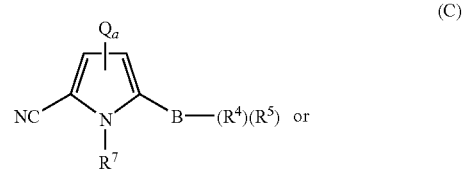

(C)

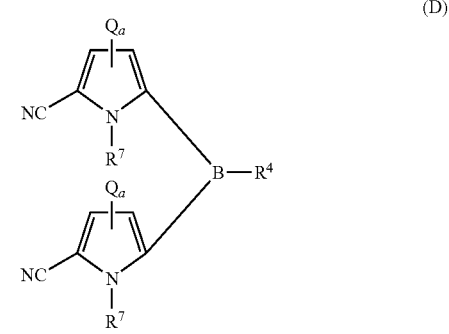

(D)

Salts of the boronic and borinic esters and the boron compounds can also independently be prepared according to the present invention and are of formulas (E), (F), (G), or (H).

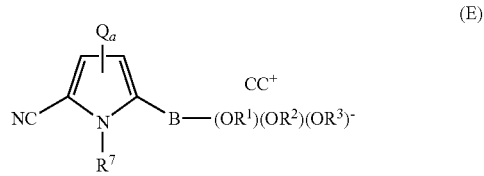

(E)

(F)

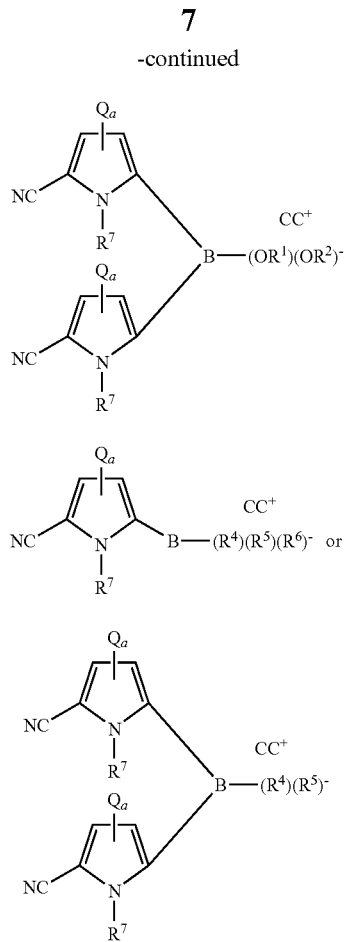

In one embodiment, $R^1$, $R^2$, and $R^3$ are selected from among $C_1$ to $C_6$ alkyl, $C_3$ to $C_8$ cycloalkyl, and hetero($C_1$ to $C_6$)alkyl. Desirably, $R^1$, $R^2$, and $R^3$ are isopropyl.

In a further embodiment, the following 2-cyanopyrrole boron-containing compounds are prepared according to the present invention. In these compounds, $CC^+$ denotes a countercation from the strong non-nucleophilic base that interacts with the base molecule to form a stable compound and Q, a, $R^7$, subst, and $CC^+$ are defined above.

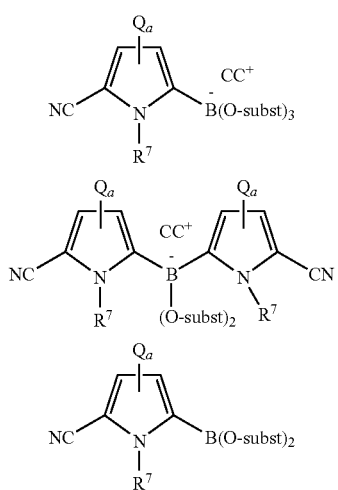

(G)

(H)

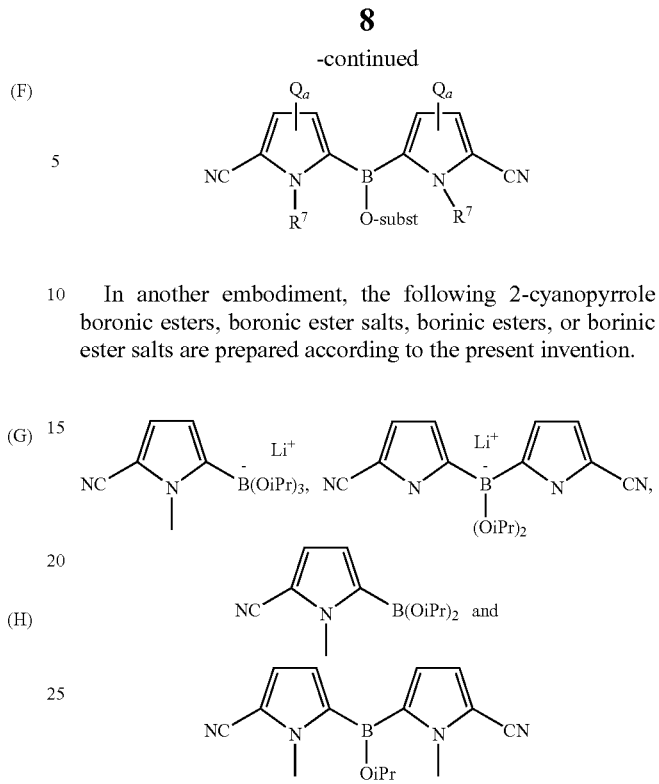

In another embodiment, the following 2-cyanopyrrole boronic esters, boronic ester salts, borinic esters, or borinic ester salts are prepared according to the present invention.

The methods for preparing boron-containing compounds, such as boronate and borinate salts, include combining a boron agent, an optionally substituted cyanopyrrole, and a strong non-nucleophilic base. See, Scheme 1, where R, subst., $R^7$, Q, a, and $CC^+$ are defined above or below.

Scheme 1

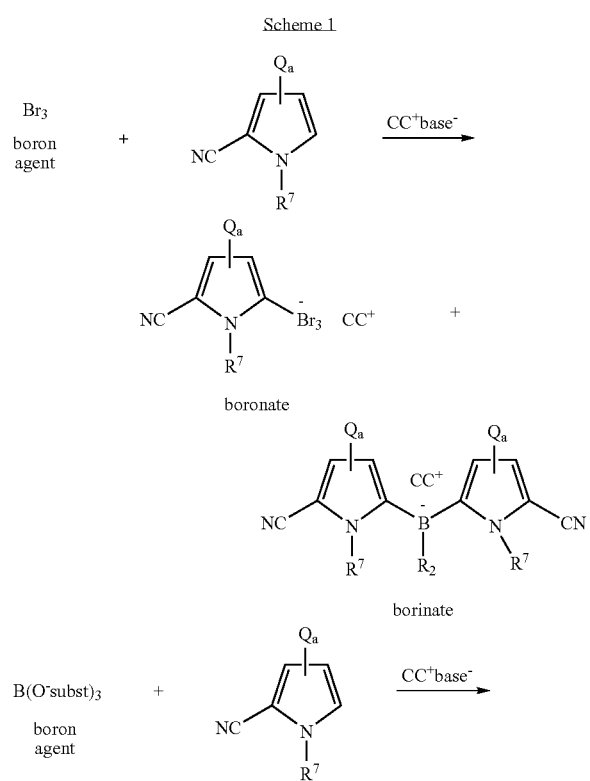

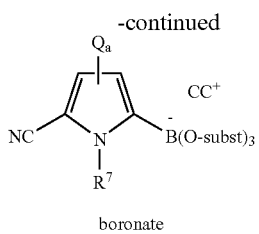

boronate

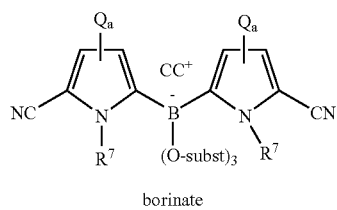

borinate

In one aspect, the boron agent is of the formula $B(OR^1)(OR^2)(OR^3)$ (depicted as $B(O\text{-subst})_3$ for convenience in Scheme 1 above). $R^1$, $R^2$, and $R^3$ are, independently, $C_1$ to $C_6$ alkyl, substituted $C_1$ to $C_6$ alkyl, $C_3$ to $C_8$ cycloalkyl, substituted $C_3$ to $C_8$ cycloalkyl, heteroaryl, substituted heteroaryl, hetero($C_1$ to $C_6$)alkyl, or substituted hetero($C_1$ to $C_6$)alkyl. In one embodiment, $R^1$, $R^2$, and $R^3$ are $C_1$ to $C_6$ alkyl. In a further embodiment, $R^1$, $R^2$, and $R^3$ are isopropyl. In yet a further embodiment, $R^1$, $R^2$, and $R^3$ are $C_3$ to $C_8$ cycloalkyl. In still another embodiment, one or more of $R^1$, $R^2$, or $R^3$ are hetero($C_1$ to $C_6$)alkyl and comprise oxygen atoms. In yet a further embodiment, $R^1$, $R^2$, or $R^3$ are, independently, $CH_2CH_2$—O—$R^{23}$, where $R^{23}$ is $C_1$ to $C_6$ alkyl, substituted $C_1$ to $C_6$ alkyl, aryl, substituted aryl, or heteroethyl groups such as —$CH_2CH_2(O$—$CH_2CH_2$—$O)_m CH_2CH_3$ and m is 1 to 8.

In another embodiment, the boron agent is of the formula $B(R^4)(R^5)(R^6)$, wherein $R^4$, $R^5$, and $R^6$ are, independently, halogen, $C_1$ to $C_6$ alkyl, or substituted $C_1$ to $C_6$ alkyl. This is depicted as $BR_3$ in the above-noted Scheme 1 for convenience.

Numerous cyanopyrroles can be used in the present invention and include N-substituted cyanopyrroles. In one embodiment, N-substituted 2-cyanopyrroles are utilized in the present invention. In another embodiment, N-alkyl-2-cyanopyrroles are utilized in the present invention. In a further embodiment, N-methyl-2-cyanopyrroles are utilized in the present invention.

In one embodiment, a cyanopyrrole of the following structure can be utilized.

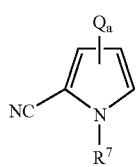

I

In formula I, $R^7$ is selected from among $C_1$ to $C_6$ alkyl, substituted $C_1$ to $C_6$ alkyl, aryl, substituted aryl, heteroaryl, substituted heteroaryl, or $COR^4$. $R^4$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. Q is selected from among H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^B$ and a is 0, 1, or 2. $R^B$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. In one embodiment, the cyanopyrrole is 1-methyl-pyrrole-2-carbonitrile The strong non-nucleophilic base must be sufficiently reactive to remove a hydrogen-atom from the pyrrole ring of the cyanopyrrole, but not react with the other substituents of the ring. A number of strong non-nucleophilic bases are known in the art and include those recited above. In one embodiment, the strong non-nucleophilic base is a lithium agent, which is desirably selected from among lithium amine salts. In one embodiment, the lithium amine salt is a dialkyl lithium amine salt, and in another embodiment, diisopropyl lithium amide (LDA).

The 2-cyanopyrrole boron-containing compounds, or derivatives thereof, are typically prepared in a solvent. Any solvent that does not react with the boron agents, the optionally substituted cyanopyrrole, strong non-nucleophilic base, or cyanopyrrole boron-containing compounds, or derivatives thereof, can be utilized. The solvent is desirably dehydrated, but can contain small amounts of water. Typically, the solvent includes an ether such as tetrahydrofuran (THF), diethylether, or combinations thereof in non-ether solvents. In one embodiment, the ether is THF or a combination of THF/heptane/ethylbenzene.

The amount of solvent utilized depends upon the scale of the reaction and the amounts of 2-cyanopyrrole, boron agent, and strong non-nucleophilic base. One of skill in the art would readily be able to determine the amount of solvent required to prepare the 2-cyanopyrrole boron-containing compounds.

III. METHODS FOR PREPARING BORONIC OR BORINIC ACIDS OR DERIVATIVES THEREOF

The present invention also provides for preparing derivatives of the borate salts including boronic acids, borinic acids, cyanopyrrole boronic acids, and cyanopyrrole borinic acids. Such boronic and borinic acids are typically isolated in situ and utilized in further reactions.

Typically, the boronic acids and borinic acids are present as a mixture of the boronic and borinic acid, optionally in the presence of residual boronic ester or salt thereof or borinic ester or salt thereof. The composition of the boronic acid/borinic acid mixture depends on the reaction conditions and can be determined by techniques known to those of skill in the art including liquid chromatography and or mass spectral analysis. For example, one mixture prepared according to the present invention contained 79.2% borinic ester (exact mass 280), 19.0% borinic acid (exact mass 238) and 1.9% boronic acid (exact mass 150).

The boronic and borinic acids can be prepared using the boronic and/or borinic esters or salts thereof as described above and hydrolyzing the same. See, Schemes 2 and 3, where $CC^+$, subst, Q, a, and $R^7$ are defined herein. Typically, hydrolyzing is accomplished using water which may contain other components including acids such as hydrochloric acid.

Scheme 2

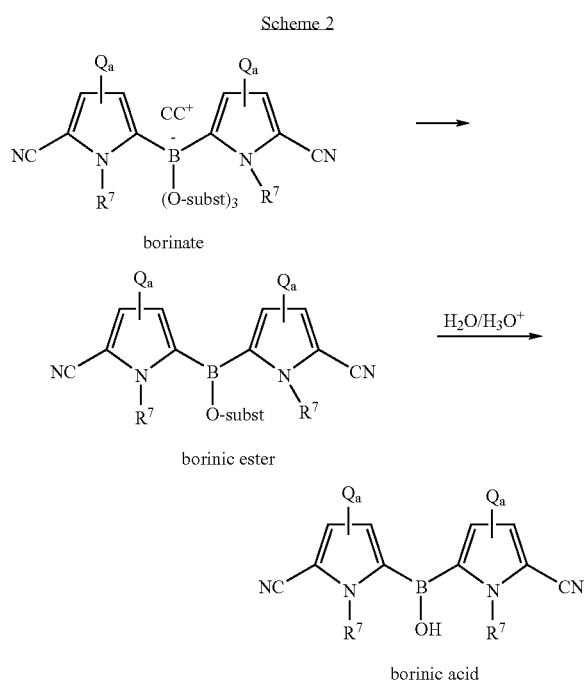

Scheme 3

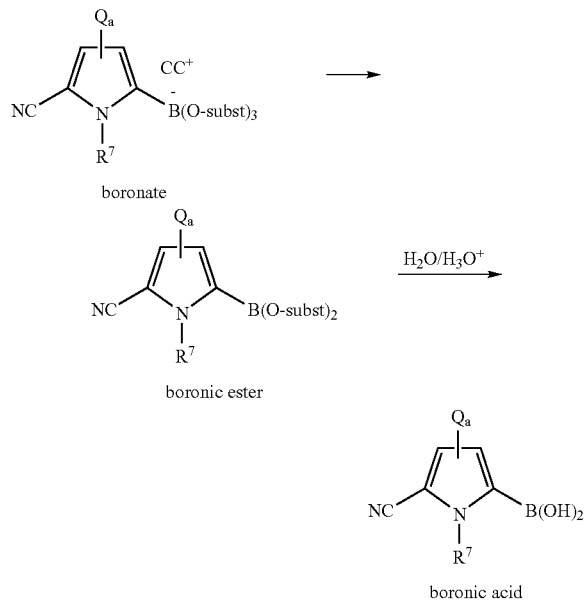

In one embodiment, the following cyanopyrrole boronic and borinic acids are prepared according to the present invention, where Q, a, and $R^7$ are defined above.

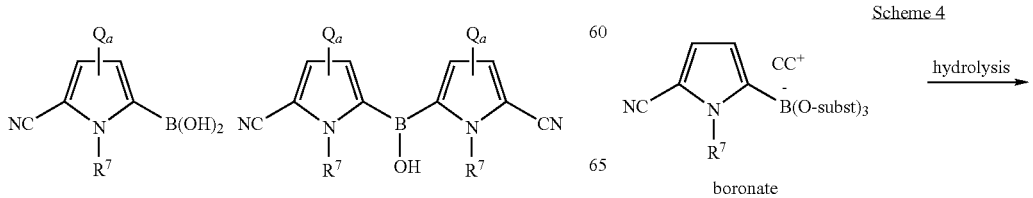

In another embodiment the following cyanopyrrole boronic and borinic acids are prepared according to the present invention.

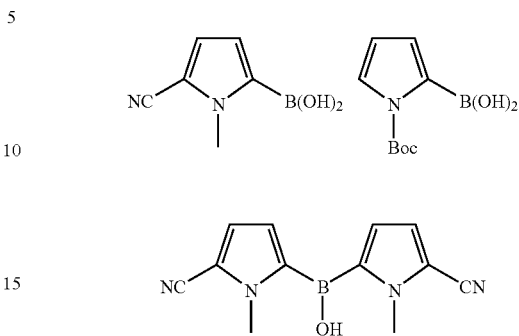

The inventors have found that cyanopyrrole boronic acid compounds can be unstable. However, without wishing to be bound by theory, the inventors have found that the formation of a boronate ester from the boronic acid stabilizes the compound, thereby permitting storage of the resulting compound at room temperature. The inventors have also hypothesized that the stability of the boronate ester can be due to the presence of an optional N-atom in the boronate ester.

The present invention therefore provides boronate esters and methods for preparing them from boronic acids. In one embodiment, the following boronate esters are prepared according to the present invention.

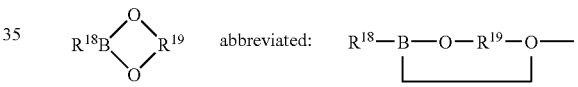

where, $R^{18}$ is selected from among 2-cyanopyrrole or substituted 2-cyanopyrrole; $R^{19}$ is selected from among $(CR^{20}R^{21})_r$ or —$(CR^{20}R^{21})_s$—$N(R^{22})$—$(CR^{20}R^{21})_t$—; s is 1, 2, 3, 4, or 5; and t is 1, 2, 3, 4, or 5. $R^{20}$ and $R^{21}$ are, independently, selected from among H, $C_1$ to $C_6$ alkyl, substituted $C_1$ to $C_6$ alkyl, aryl, and substituted aryl. $R^{22}$ is selected from among H, $C_1$ to $C_6$ alkyl, substituted $C_1$ to $C_6$ alkyl, $C_2$ to $C_6$ alkenyl, substituted $C_2$ to $C_6$ alkenyl, aryl, and substituted aryl. Desirably, $R^{19}$ is —$CH_2CH_2CH_2$—, —$CH(CH_3)CH_2$—, —$C(CH_3)_2CH_2$—, —$C(CH_3)_2CH(CH_3)$—, or —$C(CH_3)_2C(CH_3)_2$—. When $R^{19}$ is —$(CR^{20}R^{21})_s$—$N(R^{22})$—$(CR^{20}R^{21})_t$—, $R^{20}$ and $R^{21}$ are desirably H, $R^{22}$ is desirably H, phenyl, or methyl, s is 2, t is 2, and $R^{18}$ is N-methyl-2-pyrrole carbonitrile. $R^{22}$ is more desirably H.

The boronate esters are prepared according to the present invention by reacting a boronic acid with a glycol or alkanolamine. See, Scheme 4.

Scheme 4

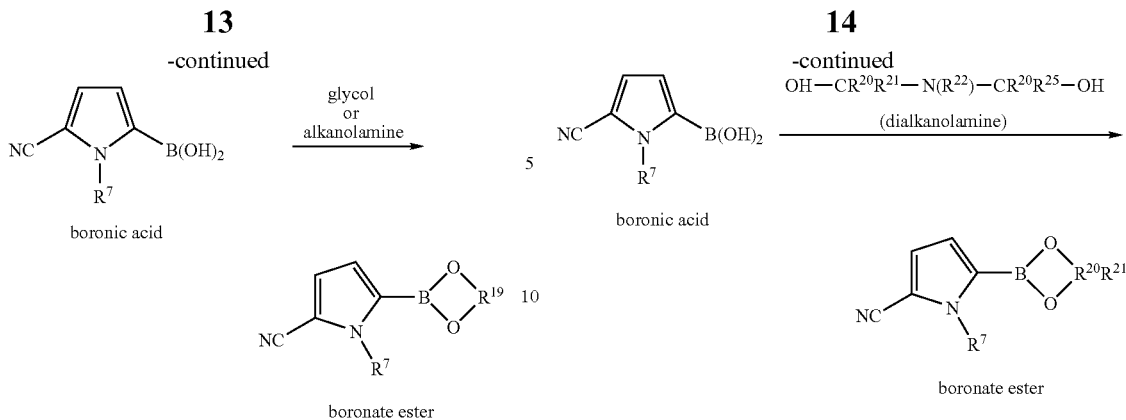

in one embodiment, the boronate ester is prepared by reacting a boronic acid with a glycol including HO—$CR^{20}R^{21}$—OH. See, Scheme 5. A variety of glycols can be utilized to prepare the boronate esters and include, without limitation, those of the formula HO—$CR^{20}R^{21}$—OH, where $R^{20}$ and $R^{21}$ are defined above. Desirably, the glycol is 1,3-propylenediol, 1,2-propylenediol, 1,2-butylenediol, 1,2-pentylenediol, or 1,2-hexylenediol.

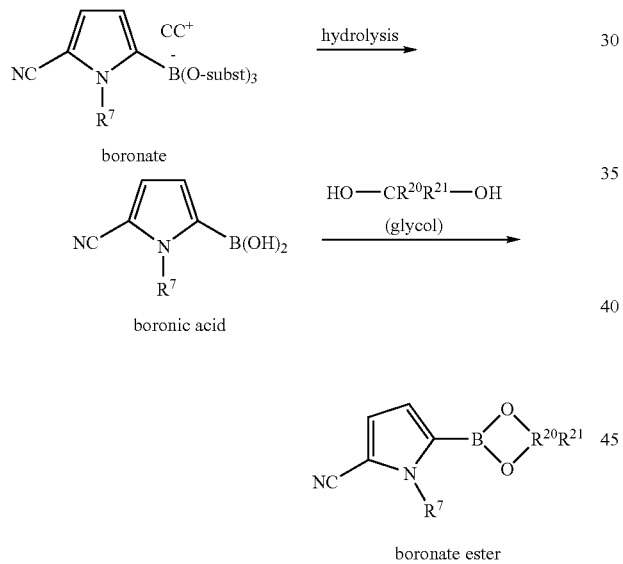

In another embodiment, the boronate ester is prepared by reacting a boronic acid with a dialkanolamine including, without limitation, HO—$CR^{20}R^{21}$—$N(R^{22})$—$CR^{20}R^{21}$—OH, where $R^{20}$, $R^{21}$, and $R^{22}$ are defined above. See, Scheme 6. Desirably, the dialkanolamine is diethanolamine.

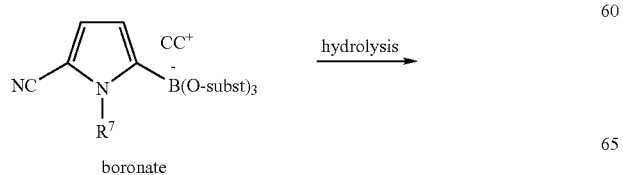

In one embodiment, the boronate ester 5-[1,3,6,2]Dioxazaborocan-2-yl-1-methyl-1H-pyrrole-2-carbonitrile is prepared according the present invention. See, Scheme 7, where $R^7$, subst, $R^{19}$, and $CC^+$ are defined above.

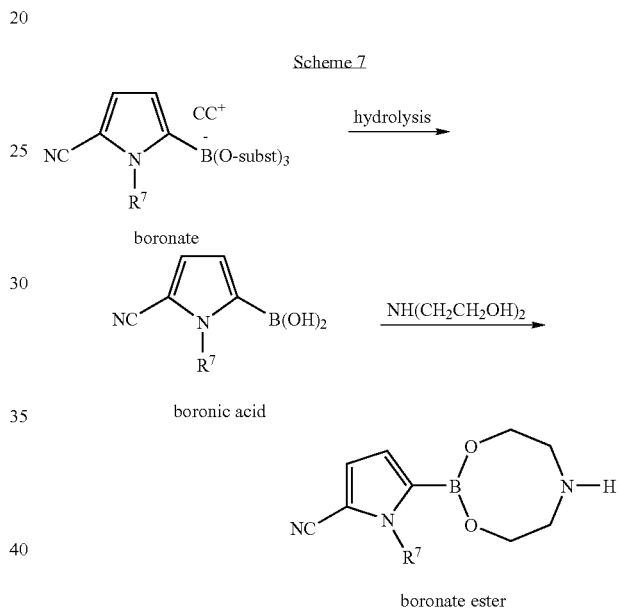

IV. METHODS OF PREPARING TRIFLUOROBORATE SALTS

The present invention further provides methods for preparing trifluoroborate salts and cyanopyrrole trifluoroborate salts by combining a fluoride agent with a boronic ester, borinic ester, or salt thereof as described above.

A number of fluoride agents can be utilized to prepare the trifluoroborate salts and include reagents such as hydrogen fluoride, or derivatives thereof including potassium hydrogen fluoride, among others. One of skill in the art would readily be able to determine a suitable fluoride agent to utilize in the present invention.

In one embodiment, the following trifluoroborate salt is prepared according to the present invention.

V. METHODS FOR COUPLING BORON-CONTAINING COMPOUNDS AND ARYL COMPOUNDS

The present invention further provides methods for coupling aryl compounds. The present invention specifically provides for coupling an aryl compound with a cyanopyrrole, and more specifically, coupling aryl compounds with cyanopyrrole boronate and borinate salts, boronic and borinic esters of salts thereof, or boronic and borinic acids as just described.

Such couplings can be performed with or without isolation of the cyanopyrrole boron-containing salts. Desirably, the cyanopyrrole boron-containing salts are not isolated and are utilized in situ in the coupling reaction.

Typically, a cyanopyrrole boron-containing salt as previously described is combined with an aryl compound and an organometallic coupling agent.

A variety of aryl compounds can be used in the present invention and include aryl compounds having a leaving group (L) attached to a carbon-atom of the aryl ring. In one embodiment, the aryl compounds have the following structure:

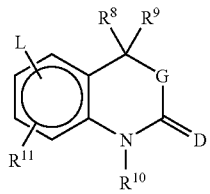

$R^8$ and $R^9$ are independently selected from among H, $C_1$ to $C_6$ alkyl, or substituted $C_1$ to $C_6$ alkyl; or $R^8$ and $R^9$ are fused to form a saturated 3 to 8 membered spirocyclic ring, a 3 to 8 membered spirocyclic ring having in its backbone at least 1 carbon-carbon double bond, or a 3 to 8 membered heterocyclic ring containing in its backbone 1 to 3 heteroatoms selected from among O, S and N. These rings are optionally substituted by from 1 to 4 groups selected from among fluorine, $C_1$ to $C_6$ alkyl, $C_1$ to $C_6$ alkoxy, $C_1$ to $C_6$ thioalkyl, $CF_3$, OH, CN, $NH_2$, NH($C_1$ to $C_6$ alkyl), or N($C_1$ to $C_6$ alkyl)$_2$. $R^{10}$ is selected from among H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, or $COR^D$. $R^D$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. $R^{11}$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. L is selected from among halogen, triflate, or a diazonium salt; G is selected from among O, S, or absent; and D is selected from among O, S, $NR^{12}$, or $CR^{13}R^{14}$. $R^{12}$ is selected from among CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heteroaryl, substituted heteroaryl, $SO_2CF_3$, $OR^{15}$ or $NR^{15}R^{16}$. $R^{13}$ and $R^{14}$ are, independently, selected from among H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heteroaryl, substituted heteroaryl, $NO_2$, CN, or $CO_2R^{17}$; $R^{15}$ and $R^{16}$ are, independently, selected from among H, $C_1$ to $C_6$ alkyl, substituted $C_1$ to $C_6$ alkyl, aryl, substituted aryl, heteroaryl, substituted heteroaryl, acyl or sulfonyl; $R^{17}$ is $C_1$ to $C_3$ alkyl; or $CR^{13}R^{14}$ is a six membered ring as shown by the structure below:

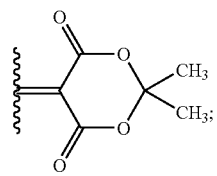

or a pharmaceutically acceptable salt thereof. Desirably, L is halogen, and more desirably L is bromine or iodine.

In a further embodiment, aryl compounds of the following structure are employed in the present invention, where $R^8$-$R^{11}$, L, G, and D are defined above.

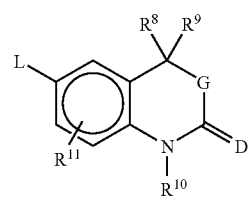

In another embodiment, aryl compounds of the following structures are used, where D and halogen are defined above.

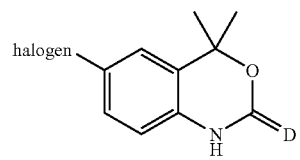

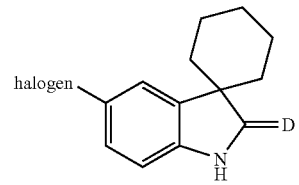

In a further embodiment, aryl compounds of the following structures are used, where D is defined above.

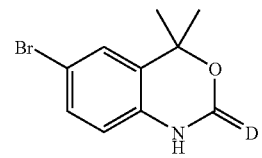

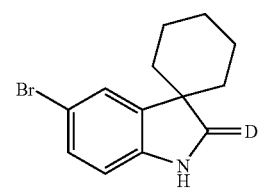

In yet another embodiment, aryl compounds of the following structures are used.

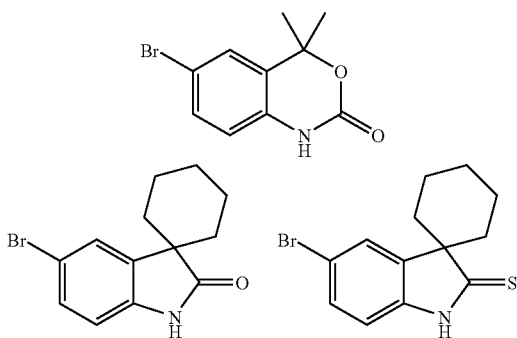

The coupling of the present invention is typically carried out in a coupling solvent. Any coupling solvent that permits coupling of the aryl compounds can be utilized and desirably includes solvents that dissolve one or more of the organometallic coupling agent, 2-cyanopyrrole boron-containing compound, and aryl compound. Desirably, the coupling solvent is maintained at about room temperature or below. The solvent is desirably dehydrated, but can contain small amounts of water. Typically, the solvent includes an ether such as THF, diethylether, and combinations thereof, and is desirably THF.

The amount of solvent utilized depends upon the scale of the reaction and specifically the amount of organometallic coupling agent, 2-cyanopyrrole, and aryl compound present in the reaction mixture. One of skill in the art would readily be able to determine the amount of solvent required to perform the coupling.

The solvent can also optionally contain additional components that do not interfere with the coupling. One of skill in the art would readily be able to determine if an additional component is adverse to the coupling reaction.

In one embodiment, the following compounds can be prepared according to the invention, where $R^7$-$R^{11}$, Q, a, D, and G are defined above.

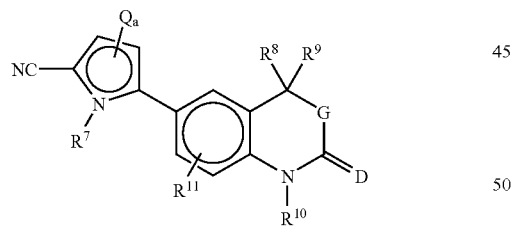

In another embodiment, the following compounds can be prepared according to the invention, where $R^8$-$R^{11}$, G, and D are defined above.

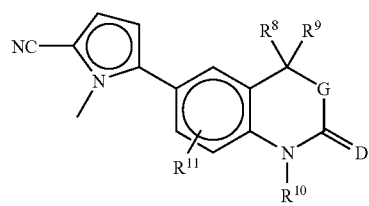

In a further embodiment, the following compounds can be prepared according to the invention, where $R^8$-$R^{10}$ are defined above.

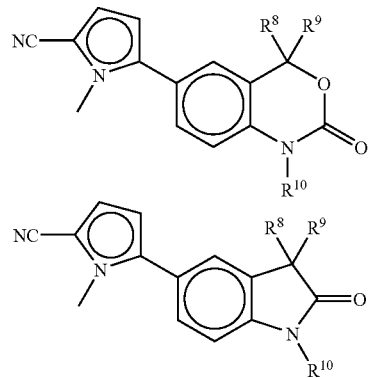

In yet another embodiment, the following compounds can be prepared according to the invention.

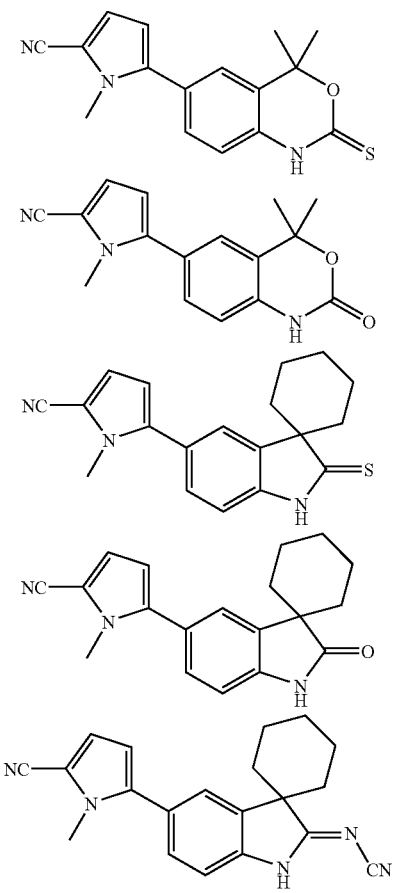

In still a further embodiment, 5-(4,4-dimethyl-2-oxo-1,4-dihydro-2H-3,1-benzoxazin-6-yl)-1H-methyl-pyrrole-2-carbonitrile is prepared according to the present invention. This process includes reacting 1-methyl-pyrrole-2-carbonitrile and a boron agent; coupling the boronated carbonitrile with 6-bromo-4,4-dimethyl-1,4-dihydro-2H-3,1-benzoxazin-2-one (the Brofoxine™ reagent) to give 5-(4,4-dimethyl-2-oxo- 1,4-dihydro-2H-3,1-benzoxazin-6-yl)-1H-methyl-pyrrole-2-carbonitrile. See, Scheme 8. Desirably, the boron agent is tri-isopropylborate. The boron agent is typically reacted with the carbonitrile in the presence of lithium di-isopropylamide (LDA) and tri-isopropylborate to give a boronate/borinate mixture which is not isolated. The coupling is typically performed in situ in the presence of a soluble palladium (0) catalyst to give 5-(4,4-dimethyl-2-oxo-1,4-dihydro-2H-3,1-benzoxazin-6-yl)-1H-methyl-pyrrole-2-carbonitrile in an unpurified form.

drofuran (THF) at a reduced temperature of about −2 to about 8° C. to give a boronate/borinate mixture. This mixture is then treated in situ with a limiting amount (about 1 equivalent) of the Brofoxine™ reagent, potassium carbonate, and tetrakis (triphenylphosphine) palladium in THF at elevated temperatures, desirably not exceeding about 70° C. to give 5-(4,4-dimethyl-2-oxo-1,4-dihydro-2H-3,1-benzoxazin-6-yl)-1H-methyl-pyrrole-2-carbonitrile in an unpurified form.

The present invention also provides a purified form of 5-(4,4-dimethyl-2-oxo-1,4-dihydro-2H-3,1-benzoxazin-6-yl)-1H-methyl-pyrrole-2-carbonitrile product. The purified form is typically prepared by adjusting the pH of the THF solution containing the 5-(4,4-dimethyl-2-oxo-1,4-dihydro-2H-3,1-benzoxazin-6-yl)-1H-methyl-pyrrole-2-carbonitrile to about 4 to about 5; removing residual palladium catalyst in the THF solution using a catalyst scavenger; removing the catalyst scavenger; exchanging the THF for a second solvent; concentrating the second solvent; precipitating the purified product; slurrying the precipitated product; and drying the purified product. See, Scheme 9. Typically, the catalyst scavenger reacts with the catalyst. In one embodiment, the catalyst scavenger is cysteine.

Scheme 8

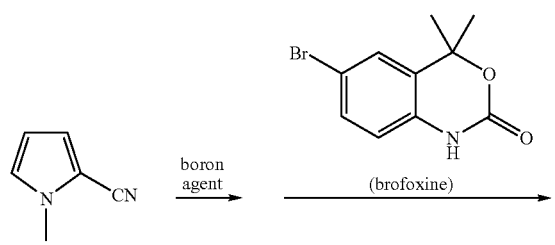

Scheme 9

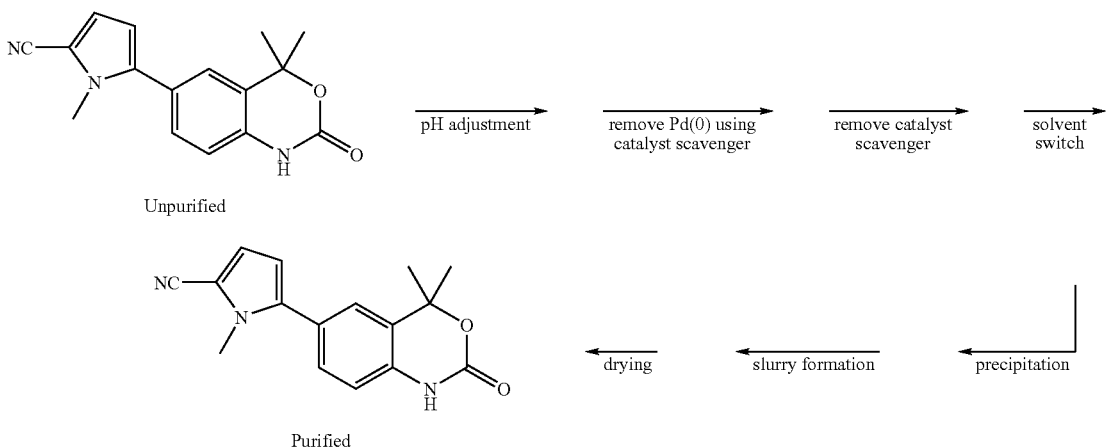

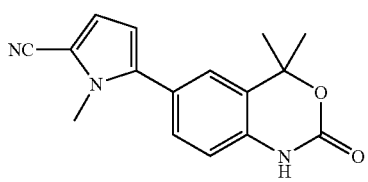

In yet another embodiment, 5-(4,4-dimethyl-2-oxo-1,4-dihydro-2H-3,1-benzoxazin-6-yl)-1H-methyl-pyrrole-2-carbonitrile is prepared by reacting 1-methyl-pyrrole-2-carbonitrile, a slight excess (about 1.3 equivalents) of lithium di-isopropylamide (LDA) and tri-isopropylborate in tetrahy- In one embodiment, purification of 5-(4,4-dimethyl-2-oxo-1,4-dihydro-2H-3,1-benzoxazin-6-yl)-1H-methyl-pyrrole-2-carbonitrile product includes washing the unpurified product with water and THF and cooling the same, desirably to 19 to 25° C.; adjusting the pH of the washed product to 4 to 5 using an acid such as hydrochloric acid or a base such as sodium hydroxide, desirably maintaining the temperature at 5 to 15° C., warming to about room temperature, and removing the aqueous phase; removing residual palladium catalyst from the organic phase, typically by adding L-cysteine and heating the mixture, desirably to 49 to 55° C.; removing excess cysteine by a route such as filtration; exchanging the solvent for toluene, desirably by distillation; concentrating the toluene solution; precipitating the product using heptane; collecting the purified precipitated product; slurrying the precipitated product in methanol; and drying the purified product, desirably at a temperature less than about 45° C.

In yet another embodiment, 5-(4,4-dimethyl-2-thioxo-1,4-dihydro-2H-3,1-benzoxazin-6-yl)-1H-methyl-pyrrole-2-carbonitrile is prepared according to the present invention. Specifically, 5-(4,4-dimethyl-2-oxo-1,4-dihydro-2H-3,1-benzoxazin-6-yl)-1H-methyl-pyrrole-2-carbonitrile is converted to the corresponding thioxo compound by reacting 5-(4,4-dimethyl-2-oxo-1,4-dihydro-2H-3,1-benzoxazin-6-yl)-1H-methyl-pyrrole-2-carbonitrile with Lawesson's reagent. See, Scheme 10.

Scheme 10

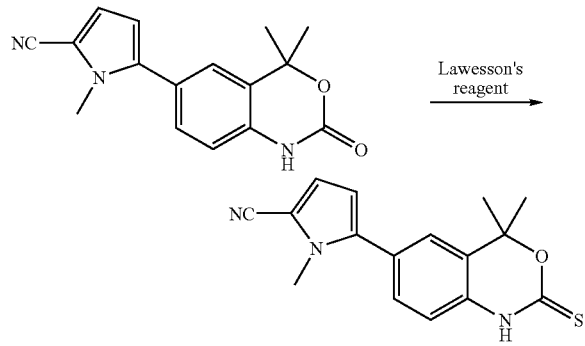

In one embodiment, 5-(4,4-dimethyl-2-thioxo-1,4-dihydro-2H-3,1-benzoxazin-6-yl)-1H-methyl-pyrrole-2-carbonitrile is prepared by reacting 5-(4,4-dimethyl-2-oxo-1,4-dihydro-2H-3,1-benzoxazin-6-yl)-1H-methyl-pyrrole-2-carbonitrile with Lawesson's reagent (about 1.1 equivalents), 1,2-dimethoxyethane (DME), and acetonitrile. Desirably, the reaction is performed at elevated temperatures such as 85 to 89° C. Typically, this reaction is permitted to progress for no more than 16 hours.

The present invention also provides for purifying 5-(4,4-Dimethyl-2-thioxo-1,4-dihydro-2H-3,1-benzoxazin-6-yl)-1H-methyl-pyrrole-2-carbonitrile. The purification includes forming a salt of the product; acidifying the salt; and isolating the acidified product, i.e., purified 5-(4,4-Dimethyl-2-thioxo-1,4-dihydro-2H-3,1-benzoxazin-6-yl)-1H-methyl-pyrrole-2-carbonitrile. See, Scheme 11.

Scheme 11

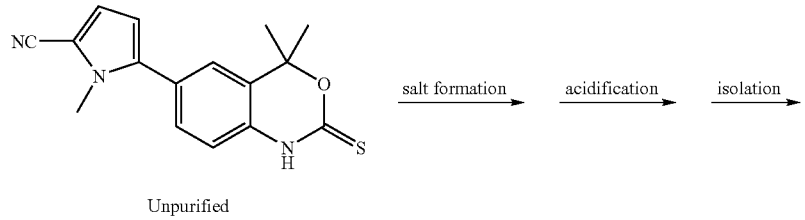 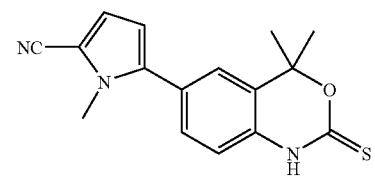

Unpurified                                                                                   Purified In one embodiment, purification of 5-(4,4-dimethyl-2-thioxo-1,4-dihydro-2H-3,1-benzoxazin-6-yl)-1H-methyl-pyrrole-2-carbonitrile includes quenching the thionation reaction with water, desirably at a temperature of about 18 to 28° C. and for at least 2 hours, slurrying the solid in water, and drying the slurried product under vacuum, desirably at room temperature for at least 12 hours; reacting the dried thioxo compound with potassium t-butoxide, desirably at 10 to 20° C. for at least 1 hour, to form the potassium salt of 5-(4,4-dimethyl-2-thioxo-1,4-dihydro-2H-3,1-benzoxazin-6-yl)-1H-methyl-pyrrole-2-carbonitrile; acidifying the potassium salt with hydrochloride acid/acetone/water, desirably at 2 to 8° C. for at least 80 minutes, to a pH of 3 to 5; dissolving the acidified salt in acetone with heating, desirably to 45 to 51° C., filtering the solution, and heating the filtered solution to reflux, precipitating solid from the heated solution with water and cooling, desirably to 2 to 8° C., and isolating the same; washing the isolated product with acetone/water; and drying the purified product at a temperature of about 35° C. and then at a temperature of less than 45° C.

VI. REAGENTS OF THE INVENTION

The compounds of the present invention, including (5-cyano-1-methyl-1H-pyrrol-2-yl) boronic acid, (5-cyano-1-methyl-1H-pyrrol-2-yl) trifluoroborate potassium salt, and 5-[1,3,6,2]Dioxazaborocan-2-yl-1-methyl-1H-pyrrole-2-carbonitrile are useful in a variety of reactions known to those of skill in the art and include those described in U.S. Pat. Nos. 6,509,334; 6,566,358; 6,391,907; 6,436,929; 6,407,101; and 6,562,857, which are herein incorporated by reference. Desirably, these compounds are useful in coupling reactions.

The compounds of the invention can be premixed in a solvent, provided that the solvent does not substantially degrade or decompose the compound, and bottled in a suitable container or kit, such as are known in the art.

Alternatively, the invention provides a container or kit whereby the compounds of the present invention are provided in a container. Such containers or kits can include the compound as a solid and optional separate aliquot of solvent required for dissolution of the solid compound.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of the Boron Containing Compounds

A. The Boronate Mixture

To a 3-L flask equipped with nitrogen inlet, pump inlet, overhead stirrer, temperature controller and a cooling bath were charged 1-methylpyrrole-2-carbonitrile (99 g, 0.933 mol), triisopropylborate (176 g, 216 mL, 0.936 mol), and THF (600 mL). After cooling the solution to about 0° C., 2M LDA (606 mL, 1.21 mol) was added in small portions, via a pump, at the rate of about 2.5 mL/min. The bath was removed and the suspension was stirred for about 1 hour at about 15° C.

B. The Trifluoroborate Salt

The boronate mixture (16 mL) prepared as described above was stirred with 5M aqueous sodium hydroxide (NaOH; 15 mL) for about 30 minutes then acidified with 10% aqueous hydrochloric acid (HCl) to a pH of about 2. Extraction with ethyl acetate and evaporation to dryness left a residue that was dissolved in methanol (MeOH; 5 mL) and treated with potassium hydrogen fluoride (KHF$_2$; 0.77 g) in water (10 mL). After stirring overnight, the yellow mixture was evaporated to dryness and extracted with hot acetone. A white precipitate was formed upon addition of ether, which was thereby filtered, washed with ether and dried to give 0.5 g of (5-cyano-1-methyl-1H-pyrrol-2-yl) trifluoroborate potassium salt. $^1$H-NMR (acetone-d$_6$): δ 6.58, 6.01, and 3.74. $^{19}$F-NMR (acetone-d$_6$): δ −141.

C. The Boronic Acid

The solution of 1-methylpyrrole-2-carbonitrile (0.131 g, 1.23 mmol), triisopropylborate (250 μL, 1.08 mmol), and THF (4 mL) was cooled to about −4° C. and 2M LDA (0.6 mL, 1.2 mmol) was added dropwise from a syringe. The bath was removed and the suspension was allowed to warm to about 13° C. within about 2 hours. After cooling and quenching with water and 5% aqueous HCl, the product was extracted with diethylether. The organic layer was evaporated to give an oil which solidified upon standing to give 0.130 g (70% yield) of (5-cyano-1-methyl-1H-pyrrol-2-yl) boronic acid. $^1$H-NMR (DMSO-d$_6$): δ 8.38, 6.87, 6.77, and 3.88.

D. Diethanolamine Ester

A 5-L flask was charged with a 2M LDA solution (800 mL, 0.16 mol) and cooled to 0 to 5° C. In a separate flask, 1-methylpyrrole-2-carbonitrile (100 g, 0.99 mol) was mixed with triisopropylborate (178 g, 0.99 mol) and diluted with THF (1 L). This solution was added into LDA over a period of 5 hours, maintaining the temperature at 0 to 5° C. Upon completion of the reaction, 4N HCl and brine (1 L, each) were added dropwise maintaining temperature at 10° C. The phases were separated and the organic phase was stirred with diethanolamine (180 g, 1.7 mol) for 1 hour. The THF was evaporated and the residue triturated with isopropanol (1 L) and the solvent was evaporated to approx. 500 mL. The resultant slurry was stirred for 30 minutes at 0 to 5° C., filtered, washed with cold isopropanol (200 mL and 100 mL) and dried in a vacuum-oven at 45° C. to give 5-[1,3,6,2]dioxazaborocyan-2-yl-1-methyl-1H-pyrrole-2-carbonitrile (155 g, 75% yield). $^1$H NMR (DMSO-d$_6$): 7.22, 6.73, 6.125, 3.9-3.75, 3.72, 3.17-3.09, and 2.9-2.8.

Example 2

SCALE-UP PREPARATION OF 5-[1,3,6,2]DIOX-AZABOROCAN-2-YL-1-METHYL-1H-PYR-ROLE-2-CARBONITRILE

In this example, a larger scale production of 5-[1,3,6,2]dioxazaborocan-2-yl-1-methyl-1H-pyrrole-2-carbonitrile was performed using the procedure of Example 1D. 1-Methylpyrrole-2-carbonitrile (6.01 kg, 56.6 mol) and triisopropyl borate (10.7 kg, 56.9 mol) were dissolved in tetrahydrofuran (48 kg). The solution was transferred into a reactor containing pre-cooled to −2° C. 2.0 M lithium diisopropylamide in heptane, ethylbenzene and THF (39.3 kg, 96.8 mol). The addition was performed over 3 hours and the reaction temperature was controlled in the range of −5 to 5° C. Following a hold of at least 30 minutes at 0 to 10° C., the batch was sampled for reaction completion analysis by high performance liquid chromatography (HPLC). Residual starting material was analyzed at 0.28%.

The reaction mixture was quenched with 4N HCl (65 kg) between 0 and 15° C. To achieve good phase separation, 18% sodium chloride brine solution (68 kg) was added, the mixture was stirred at 16 to 21° C. for an hour, then allowed to settle for 20 minutes. The lower aqueous phase was drained into a drum and diethanolamine (10.9 kg, 104 mol) was added to the organic phase over 30 minutes. A large amount of the solvent was removed by vacuum distillation at about 160 mm Hg absolute pressure and a batch temperature range of 30 to 37° C. Isopropanol (47 kg) was added to the concentrate as a replacement solvent for THF and for product crystallization. The reactor was heated back up and the process mixture concentrated to the same volume endpoint by vacuum distillation at about 110 mm Hg absolute pressure and 38 to 43° C. The concentrate was cooled to 25° C. and the resulting slurry was filtered. The cake was washed with cold isopropanol (24 kg) and dried with a nitrogen purge. The cake was further dried under vacuum at 45° C. to give 8.27 kg (66.7% yield) of the product.

Example 3

Coupling Using the Boronate Salt Mixture

A 5-L, 4-necked flask equipped with nitrogen inlet, overhead stirrer, reflux is condenser, pump inlet and temperature controller was charged with THF (600 mL), the Brofoxine™ reagent (128 g, 0.500 mol), solution of potassium carbonate (132 g, 0.955 mol) in water (460 mL), and tetrakis(triphenylphosphine)palladium (1.2 g, 0.001 mol). The suspension was heated to about 65° C. and the boronate mixture of Example 1 was added in small portions at a rate of about 5 mL/min. The reaction mixture was cooled to about 10° C. and treated, in small portions, with concentrated HCl (300 mL) to a pH of about 4 to about 5. Water (1.0 L) was added and the phases were separated. The organic phase was diluted with THF (300 mL). The Darco® KB clearing aid (12.0 g) was added and the mixture was filtered through a pad of the Celite® reagent. After washing the cake with THF (300 mL), the filtrate was distilled under vacuum to about one-fourth of the original volume (about 0.7 L). Toluene chase left a yellow suspension. Heptane (1.0 L) was added to complete precipitation of the yellow solid. The solids were filtered, washed with mother liquor and slurried in methanol (200 mL). Filtration, followed by drying gave the desired product (120 g, 85% yield, purity 98.8% HPLC area, mp 222.8° C.).

Example 4

Coupling Using the Trifluoroborate Salt

5-Bromo-(spiro[cyclohexane-1,3'-[3H]indol])-2'-ylidene-cyanamide (3.0 g, 9.86 mmol), the trifluoroborate salt (2.1 g, 9.90 mmol) prepared as described in Example 1, potassium carbonate (4.2 g, 30 mmol), and tetrakis(triphenylphosphine) palladium (24 mg) are refluxed in water (5 mL) and THF (10 mL) for about 11 hours. The reaction mixture is cooled to ambient temperature, quenched with water and acidified with HCl to a pH of about 3. The solids are filtered, washed with water, isopropanol and dried to give 5'-(5-Cyano-1-methyl-1H-pyrrol-2-yl)-spiro[cyclohexane-1,3'-[3H]indol]-2'-ylidene-cyanamide.

Example 5

Coupling Using the Diethanolamine Ester

A 3-L flask was charged with 5'-bromospiro[cyclohexane-1,3'-indol]-2'(1'H)-one (100 g, 0.357 mol), DME (750 mL), and a solution of potassium carbonate (99 g, 0.713 mol) in water (0.5 L). 5-[1,3,6,2]Dioxazaborocan-2-yl-1-methyl-1H-pyrrole-2-carbonitrile (118 g, 0.536 mol) was added followed by a solution of tetrakis(triphenylphosphine)palladium catalyst (5 g, 0.0043 mol) in DME (100 mL). The reaction mixture was stirred at reflux for 2 hours, concentrated and treated with 4N HCl (375 mL) at 5 to 10° C. Isopropanol (1 L) was added to form a suspension that was filtered, washed with isopropanol (3×0.5 L), and dried in a vacuum oven at 50 to 55° C. to give 5-(spiro[cyclohexane-1,3'-[3H]indole]-2'-oxo-5'-yl)-1H-pyrrole-1-methyl-2-carbonitrile (91 g, 83.5% yield, purity 98.7% HPLC area).

Example 6

PREPARATION OF 5-(SPIRO[CYCLOHEXANE-1,3'-[3H]INDOLE]-2'-OXO-5'-YL)-1H-PYRROLE-1-METHYL-2-CARBONITRILE

In this example, a larger scale production of 5-(spiro[cyclohexane-1,3'-[3H]indole]-2'-oxo-5'-yl)-1H-pyrrole-1-methyl-2-carbonitrile was performed using the procedure of Example 5.

5'-Bromospiro[cyclohexane-1,3'-indol]-2'(1'H)-one (7.99 kg, 28.53 mol) was charged and stirred with 1,2-dimethoxyethane (59 kg). To this solution was added a 16.5% potassium carbonate solution (48 kg, 57 mol). The batch temperature was adjusted to 25° C. and 5-[1,3,6,2]dioxazaborocan-2-yl-1-methyl-1H-pyrrole-2-carbonitrile (9.46 kg, 43.2 mol) and tetrakis(triphenylphosphine)palladium(0) catalyst (0.40 kg, 0.35 mol) were added. The mixture was heated to reflux at about 80° C. and held at reflux for 2 hours. The solution was then analyzed for the presence of starting material and showed 0.9% starting material, indicating completion of the reaction. Most of the solvent was removed by atmospheric distillation and the batch was cooled to below 10° C. A 4N HCl solution (36 kg) was added to the batch over about 0.5 hours while the batch temperature was controlled at 8 to 11° C. To the acidified mixture was charged isopropanol (63 kg) and the batch temperature was adjusted to about 10° C. The batch was filtered, washed with isopropanol (31 kg) and blown with nitrogen. The filter cake was further dried in a vacuum oven at 55° C. to furnish 9.63 kg of the crude product.

The crude product (8.61 kg, 28.2 mol) and N-acetyl-L-cysteine (2.21 kg, 13.5 mol) were charged with tetrahydrofuran (108 kg). To assure complete complexing of residual palladium, the solution was stirred overnight at 20° C. The batch was clarified through a Celite® pre-coated filter and then through a 0.2-micron Polypure DCF cartridge filter. The clarified solution was brought to reflux and distilled at ambient pressure until a landmark at 43 L residual volume was reached. The distillation temperature ranged from 67 to 70° C. To the concentrate was added isopropanol (68.5 kg) and the distillation resumed to reduce batch volume to the earlier landmark. The distillation temperature ranged from 77 to 83° C. A second aliquot of isopropanol (68 kg) was added and the distillation repeated at a temperature of 83 to 85° C. The batch was evaluated for residual solvent analysis by GC to verify THF removal; a THF/IPA weight ratio of 0.02 was found, confirming that the conditions ensured adequate THF removal. The batch was cooled to 24° C. over 1.2 hours. The batch was further cooled to 11° C. and stirred for a minimum of 0.5 hours at the same temperature. The resulting slurry was filtered, the filter cake was washed with isopropanol (13 kg) and blown on the filter with nitrogen. The wet cake was further dried under vacuum at 50° C. to a constant weight. The dry product weight was 6.50 kg for an overall yield of 83.5% (99.8% purity by HPLC area, 0.04% largest single impurity).

Example 7

PREPARATION OF 5-(4,4-DIMETHYL-2-OXO-1,4-DIHYDRO-2H-3,1-BENZOXAZIN-6-YL)-1H-METHYL-PYRROLE-2-CARBONITRILE

1-Methylpyrolle-2-carbonitrile (16.5 kg, 1.86 eq.), tri-isopropyl borate (29.3 kg, 1.88 eq.) and THF (88.9 kg) were combined and cooled to −10 to −4° C. LDA (82.0 kg) was added over at least 11 hours while maintaining the reaction temperature at −2 to 8° C. throughout the addition. High performance liquid chromatography (HPLC) was utilized to detect completion of the reaction. Once completed, the boronate intermediate was rinsed with THF (2.96 kg) and the mixture heated to 5 to 11° C.

The Brofoxine™ reagent (21.3 kg, 1.0 eq.), THF (76.9 kg) and a potassium carbonate/water solution (22.0 kg; 76.7 kg respectively) were combined under an atmosphere of nitrogen. Tetrakis(triphenylphosphine) palladium (0) (0.386 kg, 0.022 eq.) in tetrahydrofuran (11.8 kg) was added to the Brofoxine™ mixture and heated to reflux.

The boronate intermediate was then added to the Brofoxine™ mixture over a period of at least 7 hours at reflux. The reaction was monitored by HPLC and addition of the Brofoxine reagent was ceased when HPLC indicated that the reaction was complete.

The mixture was then rinsed using THF (21.3 kg) and cooled to 19 to 25° C. THF (94.4 kg) and water (157 kg) were added, the mixture stirred until all of the solid material dissolved or was suspended, and the mixture cooled to 5 to 11° C. The pH of the mixture was adjusted to a pH of 4 to 5 using hydrochloric acid (about 74.0 kg) or sodium hydroxide, which maintaining a temperature of 5 to 15° C. The mixture was rinsed using water (2.0 kg), then heated to 19 to 25° C. for at least 30 minutes with stirring, and then settled for at least 30 minutes.

L-Cysteine (3.55 kg) and THF (10.8 kg) were added to the organic layer, THF (2.0 kg) added, and the mixture heated to 49 to 55° C. for at least 12 hours. The L-cysteine was removed by filtration and the filtrate rinsed with THF (44.4 kg).

Toluene was then added (144 kg), the mixture concentrated under reduced pressures at a temperature of less than 45° C. to a volume of 121±20 liters. A second aliquot of toluene (72.5 kg) was added, the mixture concentrated under reduced pressure at a temperature of less than 45° C. to a volume of 121±20 liters. The temperature was adjusted to 19 to 25° C. Heptane (114 kg) was added and the mixture stirred for at least 60 minutes. The mixture was the filtered and the filter cake slurried with methanol (42.6 kg) until the Brofoxine™ reagent was removed. The wet cake was dried at less than 45° C.

Example 8

PREPARATION OF 5-(4,4-DIMETHYL-2-THIOXO-1,4-DIHYDRO-2H-3,1-BENZOXAZIN-6-YL)-1H-METHYL-PYRROLE-2-CARBONITRILE 5-(4,4-Dimethyl-2-oxo-1,4-dihydro-2H-3,1-benzoxazin-6-yl)-1H-methyl-pyrrole-2-carbonitrile (14.5 kg), Lawesson's Reagent (12.1 kg, 1.16 eq.), DME (215 kg), and acetonitrile (8.96 kg) were combined and heated to reflux for at least 4 hours at less than 16 hours to form unpurified 5-(4,4-dimethyl-2-thioxo-1,4-dihydro-2H-3,1-benzoxazin-6-yl)-1H-methyl-pyrrole-2-carbonitrile. The mixture was cooled to 18 to 28° C., quenched with water (276 kg), cooled to 10 to 20° C., stirred for at least 30 minutes, and the resulting slurry collected via filtration.

The wet cake was slurried in water (62.3 kg) for at least 2 hours, the slurry collected via filtration, and the wet cake washed with a second aliquot of water (20.7 kg). The resulting wet solid was dried under nitrogen and vacuum at room temperature for at least 12 hours.

The unpurified 5-(4,4-dimethyl-2-oxo-1,4-dihydro-2H-3,1-benzoxazin-6-yl)-1H-pyrrole-2-carbonitrile was then purified by dissolving the product in THF (61.4 kg) at 19 to 25° C. until a solution was obtained, which was then cooled to 12 to 18° C. A slurry of potassium-t-butoxide (17.4 kg) and tetrahydrofuran (61.4 kg) was then added while maintaining a temperature of 10 to 20° C., THF (30.7 kg) was added, and the mixture stirred at 10 to 20° C. for at least 60 minutes. The resulting slurry was filtered and the resultant filter cake washed three times with THF (36.8 kg each).

The filter cake was then dissolved in aqueous acetone (48.3 kg water; 38.3 kg acetone) at 19 to 25° C. until a solution was obtained and the solution cooled to 2 to 8° C. A 10% hydrochloric acid solution (34.7 kg water; 16.1 kg hydrochloric acid) was then added over at least 80 minutes. A temperature of 2 to 8° C. was maintained until a pH of 3 to 5 was achieved. The mixture was then stirred at 2 to 8° C. for at least 30 minutes and filtered. The filter cake was washed three times with water (18.4 kg each) and dried at less than 45° C.

The dried filter cake was then dissolved in acetone (94.4 kg) and the mixture heated to 45 to 51° C. until the solid had dissolved. The solution was then filtered through a 10 micron filter, the filter rinsed with acetone (13.5 kg), and the solution heated to reflux to remove about 113 liters of acetone by distillation. The concentrated solution was then maintained at reflux and water (56.6 kg) was added at a rate which maintains reflux. The mixture was then cooled to 2 to 8° C. at a rate of not more than 0.5° C. per minute.

The cooled mixture was then stirred at 2 to 8° C. for at least 60 minutes and filtered. The filter cake was washed three times with aqueous acetone (3.39 kg water; 2.68 kg acetone each). The washed solid was pre-dried at less than 35° C. for at least 4 hours and then dried at less than 50° C. to obtain purified 5-(4,4-dimethyl-2-thioxo-1,4-dihydro-2H-3,1-benzoxazin-6-yl)-1H-pyrrole-2-carbonitrile.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method of preparing 5-(4,4-dimethyl-2-thioxo-1,4-dihydro-2H-3,1-benzoxazin-6-yl)-1H-methyl-pyrrole-2-carbonitrile comprising:
   (a) reacting 1-methyl-pyrrole-2-carbonitrile, lithium di-isopropylamide and tri-isopropylborate;
   (b) reacting the product of step (a) with 6-bromo-4,4-dimethyl-1,4-dihydro-2H-3,1-benzoxazin-2-one, potassium carbonate, and a soluble palladium (0) catalyst;
   (c) washing the 5-(4,4-dimethyl-2-oxo-1,4-dihydro-2H-3,1-benzoxazin-6-yl)-1H-methyl-pyrrole-2-carbonitrile with water and THF;
   (d) adjusting the pH of the product of step (c) to 4 to 5;
   (e) adding L-cysteine to the product of step (d);
   (f) removing excess cysteine;
   (g) exchanging the THF for toluene;
   (h) precipitating the product of step (g); and
   (i) drying the purified 5-(4,4-dimethyl-2-oxo-1,4-dihydro-2H-3,1-benzoxazin-6-yl)-1H-methyl-pyrrole-2-carbonitrile; and
   (j) reacting said purified 5-(4,4-dimethyl-2-oxo-1,4-dihydro-2H-3,1-benzoxazin-6-yl)-1H-methyl-pyrrole-2-carbonitrile and Lawesson's reagent.

2. The method according to claim 1, further comprising:
   (a) forming a salt of 5-(4,4-dimethyl-2-thioxo-1,4-dihydro-2H-3,1-benzoxazin-6-yl)-1H-methyl-pyrrole-2-carbonitrile;
   (b) acidifying the product of step (a);
   (c) dissolving the product of step (b) in acetone;
   (d) precipitating the product of step (c); and
   (e) drying the product of step (d).

3. The method according to claim 2, wherein step (a) is performed with potassium t-butoxide.

* * * * *